(12) United States Patent
Sander

(10) Patent No.: US 9,757,244 B2
(45) Date of Patent: Sep. 12, 2017

(54) TARGETED SCREW FOR TALAR DOME FIXATION

(71) Applicant: Wright Medical Technology, Inc., Memphis, TN (US)

(72) Inventor: Elizabeth J. Sander, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 99 days.

(21) Appl. No.: 14/421,696

(22) PCT Filed: Jan. 12, 2015

(86) PCT No.: PCT/US2015/011020
§ 371 (c)(1),
(2) Date: Feb. 13, 2015

(87) PCT Pub. No.: WO2016/114751
PCT Pub. Date: Jul. 21, 2016

(65) Prior Publication Data
US 2016/0338841 A1 Nov. 24, 2016

(51) Int. Cl.
*A61F 2/42* (2006.01)
*A61B 17/16* (2006.01)
(Continued)

(52) U.S. Cl.
CPC ........ *A61F 2/4202* (2013.01); *A61B 17/1739* (2013.01); *A61B 17/1682* (2013.01); *A61B 17/1775* (2016.11); *A61F 2002/30884* (2013.01); *A61F 2002/30892* (2013.01); *A61F 2002/30899* (2013.01); *A61F 2002/4207* (2013.01)

(58) Field of Classification Search
CPC ... A61F 2002/30902; A61F 2002/4207; A61B 2017/1775
See application file for complete search history.

(56) References Cited

U.S. PATENT DOCUMENTS 4,021,864 A  5/1977  Waugh
4,232,404 A * 11/1980  Samuelson ........... A61F 2/4202
                                                       623/21.18
(Continued)

FOREIGN PATENT DOCUMENTS

DE  19949890 A1  6/2001
EP  2363087 B1   5/2014
(Continued)

OTHER PUBLICATIONS

Translation of FR2776506A1 retrieved from Espacenet on Oct. 13, 2016.*
(Continued)

*Primary Examiner* — Thomas J Sweet
*Assistant Examiner* — Megan Wolf
(74) *Attorney, Agent, or Firm* — Duane Morris LLP

(57) ABSTRACT

A bone implant is disclosed. The implant comprises a body having a bone contact surface and an articulation surface. A first flange extends longitudinally from the bone contact surface. The flange defines a first screw hole configured to receive a targeted screw therethrough. The targeted screw couples the implant to a bone.

14 Claims, 5 Drawing Sheets

(51) Int. Cl.
*A61B 17/17* (2006.01)
*A61F 2/30* (2006.01)

(56) References Cited

U.S. PATENT DOCUMENTS

| | | | | |
|---|---|---|---|---|
| 5,344,458 | A | * 9/1994 | Bonutti | A61B 17/863 |
| | | | | 623/20.32 |
| 6,458,136 | B1 | * 10/2002 | Allard | A61B 17/1684 |
| | | | | 606/92 |
| 6,663,669 | B1 | 12/2003 | Reiley | |
| 8,303,667 | B2 | 11/2012 | Younger | |
| 8,585,744 | B2 | 11/2013 | Duggal et al. | |
| 8,715,363 | B2 | 5/2014 | Ratron et al. | |
| 2002/0055744 | A1 | * 5/2002 | Reiley | A61B 17/15 |
| | | | | 606/79 |
| 2006/0149387 | A1 | * 7/2006 | Smith | A61F 2/4081 |
| | | | | 623/19.11 |
| 2007/0299522 | A1 | 12/2007 | Gill | |
| 2008/0103603 | A1 | 5/2008 | Hintermann | |
| 2010/0016972 | A1 | 1/2010 | Jansen et al. | |
| 2010/0057216 | A1 | 3/2010 | Gannoe et al. | |
| 2011/0035019 | A1 | 2/2011 | Goswami et al. | |
| 2011/0166608 | A1 | 7/2011 | Duggal et al. | |
| 2012/0010718 | A1 | 1/2012 | Still | |
| 2012/0109320 | A1 | * 5/2012 | Walch | A61F 2/4081 |
| | | | | 623/19.11 |
| 2014/0128985 | A1 | 5/2014 | Sanders et al. | |
| 2014/0257495 | A1 | 9/2014 | Goldberg | |

FOREIGN PATENT DOCUMENTS

| | | | | |
|---|---|---|---|---|
| FR | 2724108 | A1 * | 3/1996 | A61F 2/4202 |
| FR | 2759900 | B1 | 6/1999 | |
| FR | 2776506 | A1 * | 10/1999 | A61F 2/4081 |

OTHER PUBLICATIONS

International Search Report and Written Opinion of the International Searching Authority issued in connection with International Application No. PCT/US2015/011020, Oct. 2, 2015, 13 pages.

Examination Report issued for corresponding Australian patent application No. 2015202181, May 10, 2016, 9 pages.

Espinosa, N. et al., "Misalignment of Total Ankle Components Can Induce High Joint Contact Pressures" J Bone Joint Surg Am, 2010, 92, pp. 1179-1187.

Extract from "Total Ankle Arthroplasty; historical overview, current concepts and future perspectives" (Beat Hintermann), Ch. 6, SpringerWien New York, 2005, pp. 70-75.

Surgical Technique Guide (newdeal and Integra LifeSciences Corporation), 2006, pp. 1-23.

Barg, A. et al., "Total Ankle Replacement Using HINTEGRA, an Unconstrained, Three-Component System", Foot Ankle Clin N Am, 2012, pp. 607-635.

Valderrabano, V. et al., "Total Ankle Replacement—Three-Component Prosthesis", Techniques in Foot and Ankle Surgery, 2005, 4(1), 42-54.

Hintermann, B. et al., "The HINTEGRA Ankle: Rationale and Short-Term Results of 122 Consecutive Ankles", Clinical Orthopaedics and Related Research, 2004, No. 424, pp. 57-68.

Surgical Technique Guide—Total Ankle System (DePuy), 2005, pp. 1-21.

BOX Advertisement (MatOrtho), BOX® Total Ankle Replacement, Part No. ML-300-037-L, Issue 1, 2 pages, Undated.

Operative Technique Guide (MatOrtho), BOX® Total Ankle Replacement, 2011, pp. 1-35.

"BOX Total Ankle Replacement" OrthopaedicsOne Articles. In: OrthopaedicsOne—The Orthopaedic Knowledge Network. Created Jul. 14, 2011 07:26. Last modified Aug. 24, 2014 13:59 ver.8. Retrieved Apr. 5, 2017, from http://www.orthopaedicsone.com/x/Pgi-Aw.

CCI Total Ankle Replacement Surgical Technique Guide (Wright Medical Technology), 2012.

Van Straten Medical CCI Evolution brochure, 2006, 10 pages.

Surgical Technical 2.0 Guide (Van Straten Medical), 2010, 20 pages.

English translation of First Office Action issued for corresponding Chinese patent application No. 201580001471.7, dated Mar. 20, 2017, 5 pages.

* cited by examiner

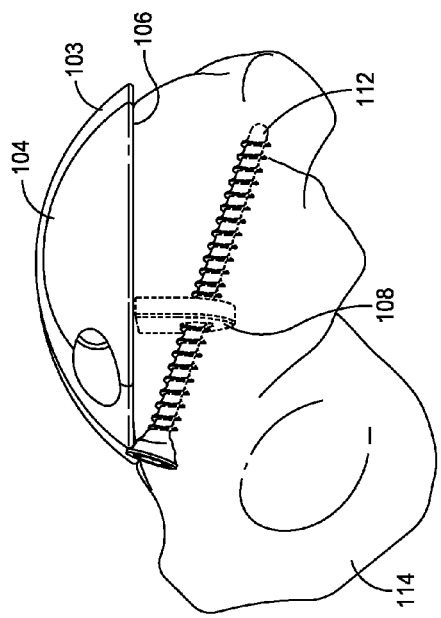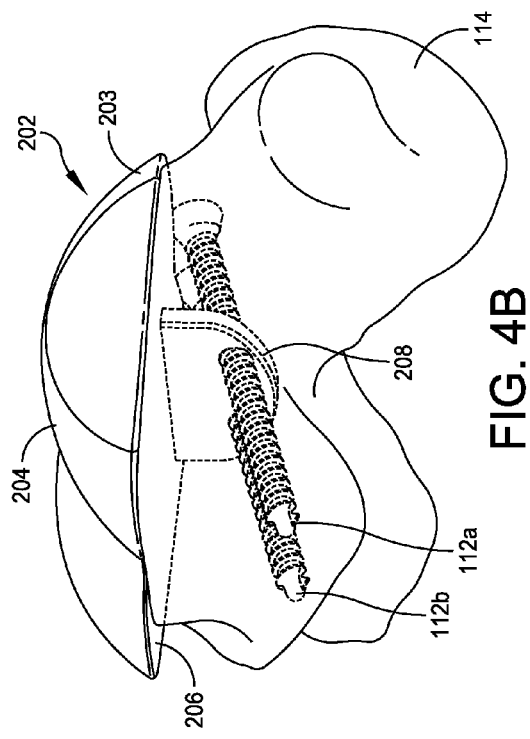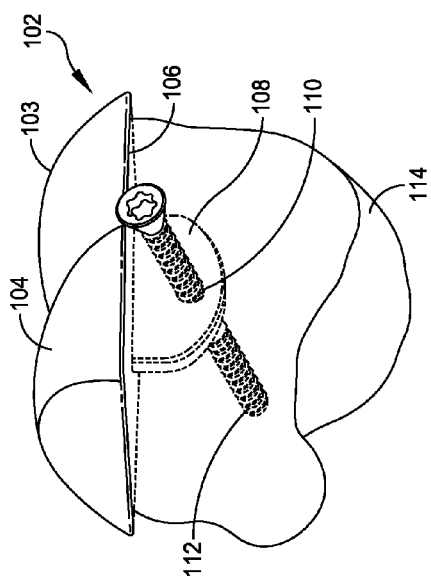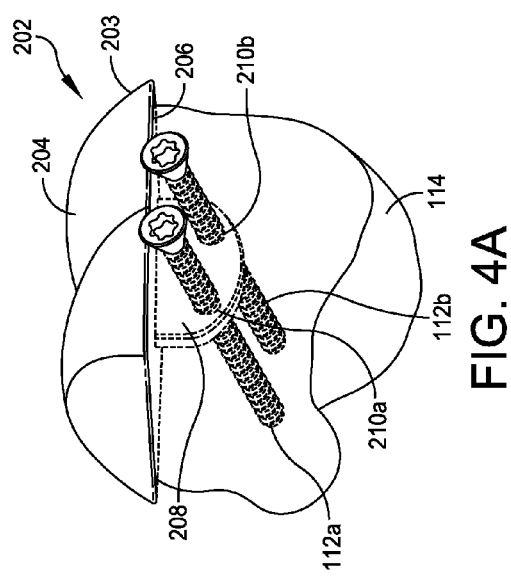

TARGETED SCREW FOR TALAR DOME FIXATION

CROSS REFERENCE TO RELATED APPLICATIONS

This application is a national phase entry under 35 U.S.C. §371 of international patent application No. PCT/US15/11020, filed Jan. 12, 2015, the entirety of which is herein incorporated by reference.

BACKGROUND

An ankle joint may become severely damaged and painful due to arthritis, prior ankle surgery, bone fracture, osteoarthritis, and/or one or more additional conditions. Options for treating the injured ankle have included anti-inflammatory and pain medications, braces, physical therapy, joint arthrodesis, and total ankle replacement.

Total ankle replacement generally comprises two components—one portion coupled to the tibia and one portion coupled to the talus. The components comprise articulation surfaces sized and configured to mimic the range of motion of the ankle joint. For example, the talar portion may comprise a component sized and configured to mimic the articulation of the talus and the tibial portion may comprise an articulation surface configured to mimic articulation of the tibia.

Installation of the total ankle replacement may comprise forming one or more holes or cuts in a bone. For example, a hole may be drilled through the talus and into the tibia to create a channel for inserting a tibial stem. In some installations, additional bone is removed from the talus to make space for a talar stem extending from the talar portion.

SUMMARY

In some embodiments, an implant is disclosed. The implant comprises a body having a bone contact surface and an articulation surface. A flange extends longitudinally from the bone contact surface. The flange defines a first screw hole configured to receive a targeted screw therethrough. The targeted screw couples the implant to a bone.

In some embodiments, a drill guide is disclosed. The drill guide comprises a first portion configured to couple to an articulation surface of an implant and a second portion extending longitudinally from the first portion. The second portion defines a first drill guide hole sized and configured to receive a drill therethrough. The drill guide positions the drill to form a pilot hole through a bone that passes through a screw hole defined by the flange of the implant.

In some embodiments, a method for coupling an implant to a bone is disclosed. The method comprises locating an implant at a predetermined location on a bone. The implant comprises a body having an articulation surface and a bone contact surface and a first flange extending longitudinally from the bone contact surface into a channel formed in the bone. The first flange defines a first screw hole. The method further comprises coupling a drill guide to the implant. The drill guide comprises a first portion configured to couple to the articulation surface of the implant and a second portion extending longitudinally from the first portion. The second portion defines at least one drill guide hole sized and configured to receive a drill therethrough. The method further comprises forming a first pilot hole through the bone and the first screw hole by inserting a drill through the drill guide hole.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 3A illustrates one embodiment of a talar dome coupled to a talus by a targeted screw.

FIG. 3B illustrates a side view of the talar dome of FIG. 3A.

FIG. 4A illustrates one embodiment of a talar dome coupled to a talus by a pair of targeted screws.

FIG. 4B illustrates a side view of the talar dome of FIG. 4A.

DETAILED DESCRIPTION

Figure 1:
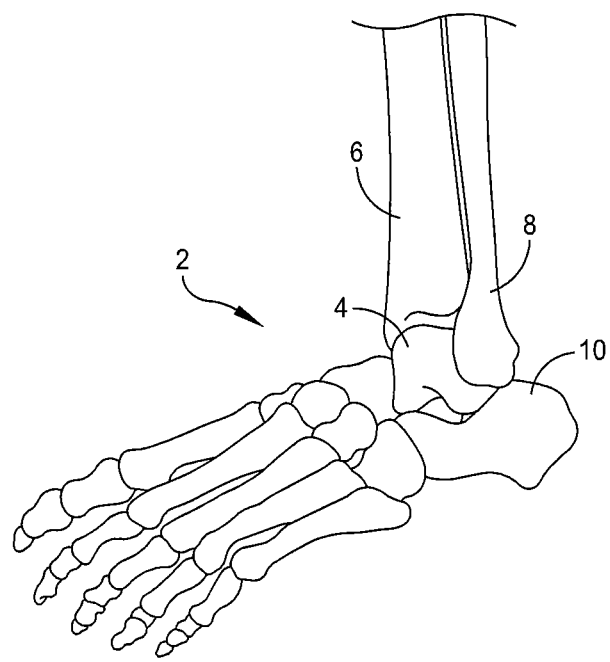
FIG. 1 illustrates an anatomic view of an ankle joint.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides a bone implant for use with a joint replacement system. The bone implant generally comprises a body having an articulation surface and a bone contact surface. A flange extends longitudinally from the bone contact surface. The flange defines a screw hole configured to receive a targeted screw therethrough.

Figure 2:
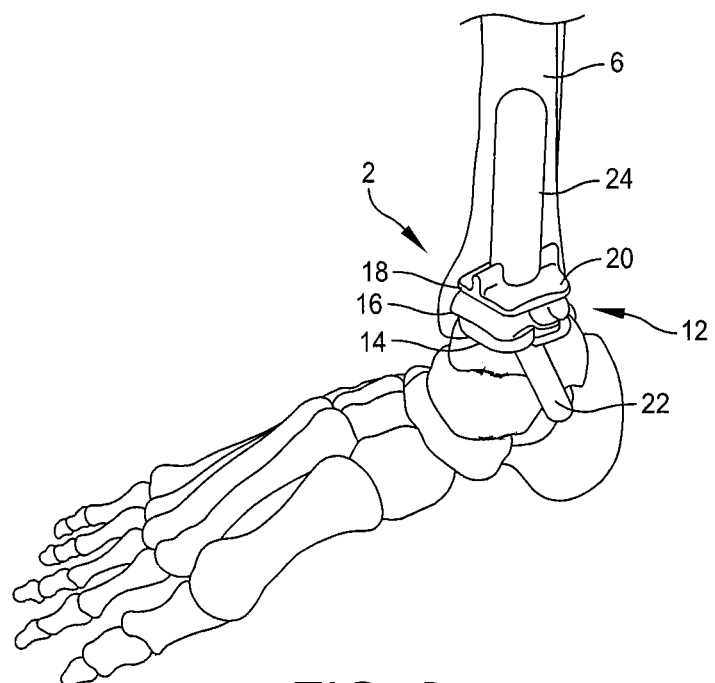
FIG. 2 illustrates one embodiment of an ankle joint having a total ankle replacement system therein.

FIG. 1 illustrates an anatomic view of an ankle joint 2. The ankle joint 2 comprises a talus 4 in contact with a tibia 6 and a fibula 8. A calcaneus 10 is located adjacent to the talus 4. In total ankle replacements, the talus 4 and the tibia 6 may be resected, or cut, to allow insertion of a talar implant and a tibial implant. FIG. 2 illustrates the ankle joint 2 of FIG. 1 having a total ankle replacement system 12 inserted therein.

The total ankle replacement system 12 comprises a talar platform 14 and a tibial platform 18. The talar platform 14 comprises a body defining a talar articulation surface 16 (or talar dome). A stem 22 (or flange) extends into the talus 4 to anchor the talar platform 14 to the talus 4. The tibial platform 18 is sized and configured for installation into the tibia 6. The tibial platform 18 comprises a body having an articulation surface 20 and a tibial stem 24 extending into the tibia 6 to anchor the tibial platform 18. The talar joint surface 16 and the tibial joint surface 20 are mutually sized and configured to articulate. The joint surfaces 16, 20 replace the natural ankle joint surfaces, which are removed, to restore a range of motion that mimics the natural joint. One or more holes may be formed in the tibia and/or the talus prior to and during insertion of the tibial implant 18 or the talar implant 12.

The joint surfaces 16, 20 may be made of various materials, such as, for example, polyethylene, high molecular weight polyethylene (HMWPE), rubber, titanium, titanium alloys, chrome cobalt, surgical steel, and/or any other suitable metal, ceramic, sintered glass, artificial bone, and/or any combination thereof. The joint surfaces 16, 20 may comprise different materials. For example, the tibial joint surface 20 may comprise a plastic or other non-metallic material and the talar joint surface 16 may comprise a metal surface. Those skilled in the art will recognize that any suitable combination of materials may be used.

FIG. 3A illustrates one embodiment of a talar implant 102 configured to receive a targeted screw 112 to anchor the talar implant 102 to a bone 114. The talar implant 102 comprises a body 103 having an articulation surface 104 and a bone contact surface 106. The articulation surface 104 is sized and configured to mimic articulation of a bone, such as, for example, a talus. The articulation surface 104 may comprise, for example, a first hemisphere and a second hemisphere configured to mimic articulation of a talar dome with respect to a tibia. The bone contact surface 106 is located opposite of the articulation surface 104 and is sized and configured to contact a resected surface of the bone 114.

The implant 102 comprises a flange 108 extending from the bone contact surface 106. The flange 108 defines a screw hole 110. The screw hole 110 is configured to receive a targeted screw 112 therethrough. The flange 108 is inserted into a channel formed in the bone 114. The channel may be formed by any suitable means, such as, for example, reaming or drilling. The targeted screw 112 is inserted into a first side of the bone 114, extends through the screw hole 110, and into a second side of the bone. The targeted screw 112 anchors the implant 102 to the bone 112. In some embodiments, the screw 112 is inserted into a pre-drilled and/or pre-tapped pilot hole. In other embodiments, the screw 112 comprises a self-drilling and/or self-tapping screw and may be driven directly into the bone 114.

FIG. 3B illustrates a side view of the implant 102 and the bone 114 coupled by the targeted screw 112. The targeted screw 112 extends from at least a first side of the bone 114, through the screw hole 110 in the flange 108, and at least partially into a second side of the bone 114. In some embodiments, the screw 112 extends through the bone 114 and into a second bone (not shown) to fuse one or more joints. For example, in one embodiment, a first bone 114 comprises a talus. The targeted screw 112 is inserted through a second bone, such as, for example, a navicular, extends through the second bone and into the first bone, and through the hole 110 in the flange 108. In another embodiment, the targeted screw extends through a first side of the first bone 114, through the hole 110 in the flange 108, through a second side of the first bone 114, and into a second bone, such as, for example, a calcaneus. Those skilled in the art will recognize that the screw 112 may comprise any suitable length for extending partially or completely through the first bone 114.

The flange 108 may comprise any suitable shape. In the illustrated embodiment, the flange 108 comprises a solid, U-shaped piece having a screw hole 110 formed therein. It will be recognized by those skilled in the art that any suitable shape, such as, for example, a square flange, a round flange, and/or any other suitably shaped flange may be used. The flange 108 extends a predetermined depth into the bone 114 sufficient to provide the screw hole 110 at a predetermined depth for receiving the targeted screw 112. For example, in some embodiments, the flange 108 may extend a depth equal to the thickness of the body 103 of the implant 102. In other embodiments, the flange 108 may extend to a greater or a lesser depth.

FIG. 4A illustrates one embodiment of an implant 202 configured to receive a pair of targeted screws 112a, 112b therethrough to anchor the implant 202 to the bone 114. The implant 202 comprises a body 203 having an articulation surface 204 and a bone contact surface 206. The articulation surface 204 is sized and configured to mimic articulation of a bone, such as, for example, a talus. The articulation surface 204 may comprise, for example, a first hemisphere and a second hemisphere configured to mimic articulation of a talar dome with respect to a tibia. The bone contact surface 206 is located opposite of the articulation surface 204 and is sized and configured to contact a resected surface of the bone 114. The implant 202 is similar to the implant 102 discussed with respect to FIGS. 3A-3B.

FIG. 4B illustrates a side view of the implant 202 anchored to the bone 114 by a pair of targeted screws 112a, 112b. The implant 202 comprises a flange 208 extending from the bone contact surface 206. The flange 208 extends a predetermined distance from the bone contact surface 206 into the bone 114. The flange 208 defines a pair of screw holes 210a, 210b configured to receive targeted screws 112a, 112b therethrough. The targeted screws 112a, 112b extend from at least a first side of the bone 114 at least partially into a second side of the bone 114. In some embodiments, one or more of the targeted screws 112a, 112b may extend through the bone 114 into one or more additional bones. In the illustrated embodiment, the pair of screw holes 210a, 210b are horizontally aligned and equally spaced on the flange 208. In other embodiments, the pair of screw holes 210a, 210b may be staggered and/or unevenly spaced on the flange 208. Although embodiments have been illustrated with a single screw hole and a pair of screw holes, it will be recognized that a flange 108, 208 may contain any suitable number of screw holes for receiving any number of targeted screws.

Figure 5B:
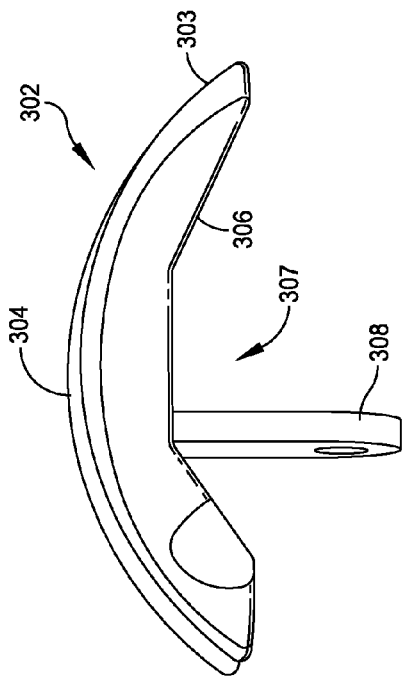
FIG. 5B illustrates a side view of the talar dome of FIG. 5A.
Figure 5A:
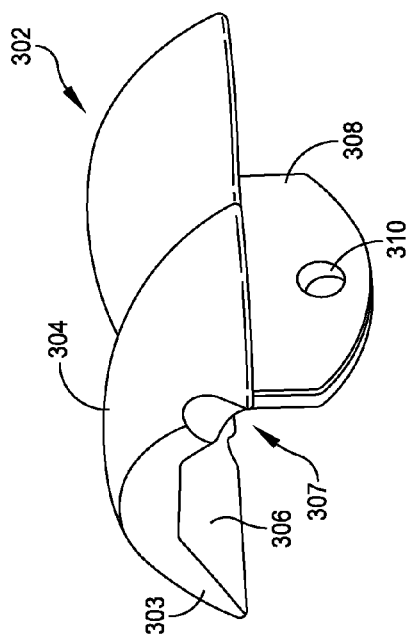
FIG. 5A illustrates an alternative embodiment of a talar dome configured to be coupled to a talus by a targeted screw.

FIGS. 5A and 5B illustrate one embodiment of an implant 302 comprising a flange 308 configured to receive a targeted screw therethrough. The implant 302 comprises a body 303 having an articulation surface 304 and a bone contact surface 306. The body 303 is concave along the bone contact surface 306 to define a cavity 307 for receiving a bone therein. The cavity 307 is sized and configured to couple to a bone, such as, for example, a resected talus. A flange 308 extends from the bone contact surface 306 and through the cavity 307. The flange 308 is sized and configured to be received within the bone. The flange 308 defines a screw hole 310 sized and configured to receive a targeted screw therethrough.

Figure 6:
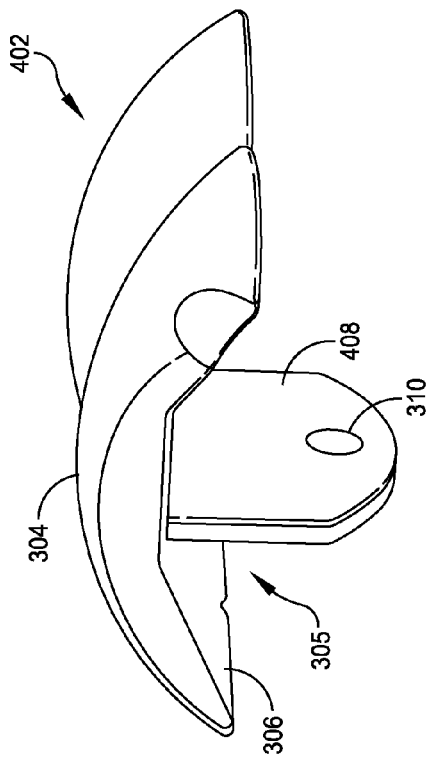
FIG. 6 illustrates one embodiment of a talar dome having a posterior flange configured to receive a targeted screw therethrough.

The flange 308 is located on an anterior section of the implant 302. The flange 308 is received within a hole formed in the bone. The hole may be cut and/or reamed prior to coupling the implant 302 to the bone. The flange 308 is sized and configured to position the screw hole 310 such that a targeted screw may be inserted into the bone to anchor the implant 302 to the bone. FIG. 6 illustrates one embodiment of an implant 402 having a flange 408 located on a posterior section of the implant 402. The implant 402 is similar to the implant 302 shown in FIGS. 5A-5B.

Figure 7:
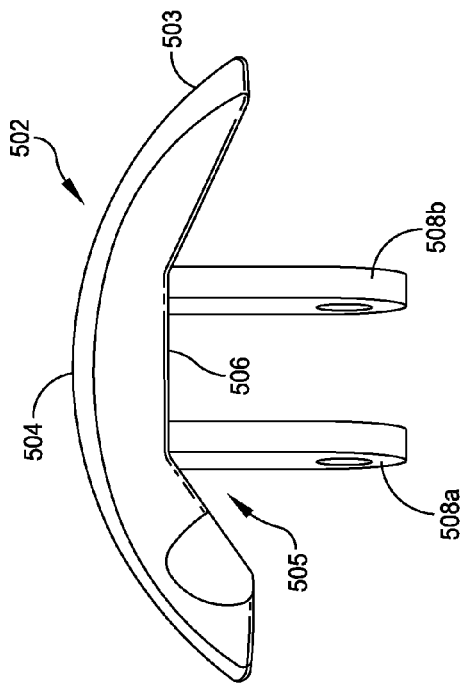
FIG. 7 illustrates one embodiment of a talar dome having an anterior flange and a posterior flange.

FIG. 7 illustrates one embodiment of an implant 502 comprising a plurality of flanges 508a, 508b for receiving targeted screws therethrough. The implant 502 is similar to the implant 302 illustrated with respect to FIGS. 5A-5B and comprises a body 503 having an articulation surface 504 and a bone contact surface 506. The bone contact surface 506 defines a concave cavity 507 for receiving a bone therein. A first flange 508a and a second flange 508b extend longitudinally from the bone contact surface 506. In the illustrated embodiment, the first flange 508a extends from an anterior portion of the implant 502 and the second flange 508b extends from a posterior portion of the implant 502. Each of the flanges 508a, 508b define at least one screw hole for receiving a targeted screw therein.

In some embodiments, a screw hole in the first flange 508a and a screw hole in the second flange 508b are aligned such that a single targeted screw extends through the screw hole in the first flange 508a and the screw hole in the second flange 508b. For example, in some embodiments, the screw hole in the first flange 508a may be located closer to the bone contact surface 506 than a screw hole in the second flange 508b. A targeted screw may extend through the hole in the first flange 508a at an angle and continue through the screw hole in the second flange 508b. In some embodiments, a screw hole in the first flange 508a receives a first targeted screw and the screw hole in the second flange 508b receives a second targeted screw.

Figure 8:
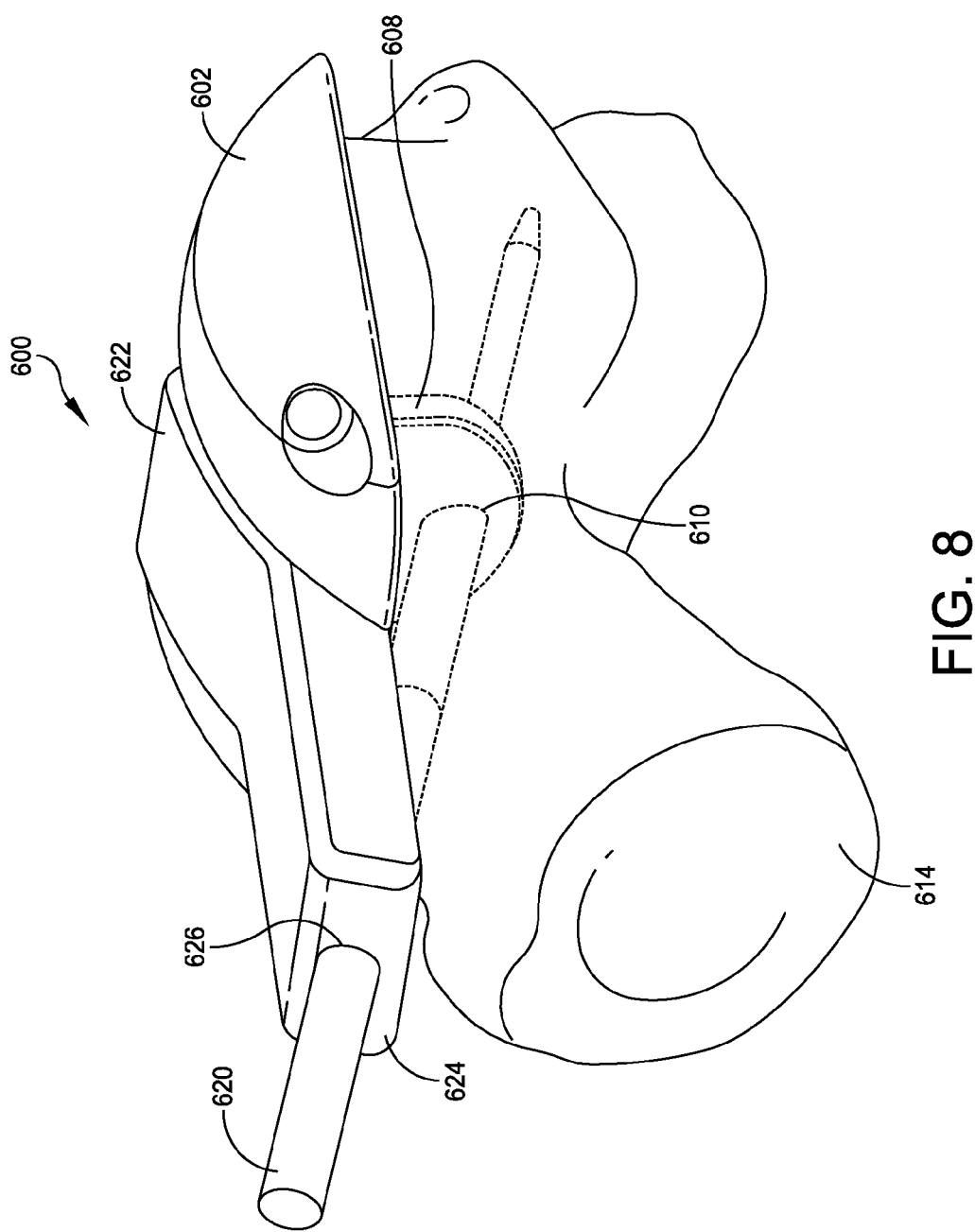
FIG. 8 illustrates one embodiment of a targeted drill guide.

FIG. 8 illustrates a targeted drill guide 600. The targeted drill guide 600 is sized and configured to guide a drill 620 through a bone 614 such that the drill 620 forms a hole through the bone 614 and a screw hole 610 in a flange 608 of an implant 602. The targeted drill guide 600 comprises a first portion 622 sized and configured to couple to the implant 602. The first portion 622 may comprise, for example, a curved section having a curvature and cross-section configured to match the curvature and cross-section of the articulation surface 604 of the implant 602. The targeted drill guide 600 further comprises a second portion 624 extending longitudinally from the first portion 622. The second portion 624 comprises a drill guide hole 626 configured to receive a drill 620 therethrough. The second portion 624 comprises a predetermined length and the drill guide hole 626 comprises a predetermined angle such that a drill 620 extending through the drill guide hole 626 will pass through the screw hole 610 in the flange 608 of the implant 602. Although the drill guide 600 is illustrated with a single guide hole 626, it will be recognized that the second portion 624 may comprise any number of drill guide holes 626 corresponding to one or more screw holes 610 in the flange 608.

Figure 9:
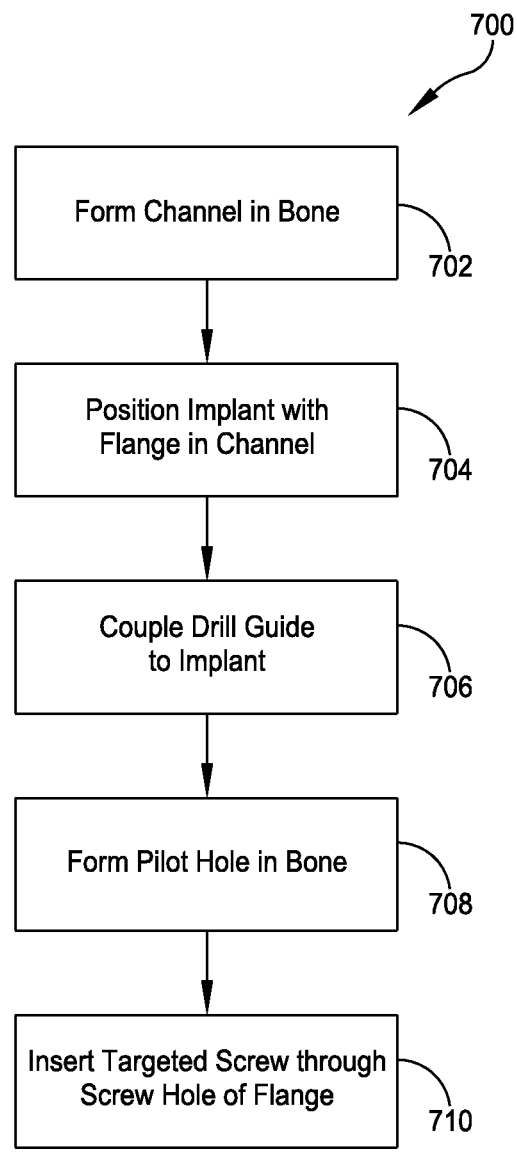
FIG. 9 is a flowchart illustrating one embodiment of a method for mounting an implant having a flange to a bone.

FIG. 9 is a flowchart illustrating one embodiment of a method 700 for mounting an implant having a flange to a bone. For example, in some embodiments, the implant 102 may be coupled to a bone 114. In a first step 702, a channel is formed in a bone 114. The channel may be formed by any suitable method such as, for example, reaming, drilling, cutting, and/or any other suitable method. The channel extends a predetermined distance into the bone 114 and may comprise a predetermined shape, such as, for example, a semi-circular shape. The channel is configured to receive a flange 108 of an implant 102.

In a second step 704, an implant is 102 located at the bone 114 and a flange 108 of the implant 108 is inserted into the channel to position the implant 102 with respect to the bone 114. The flange 108 is sized and configured to be received within the channel formed in the bone 114. In a third step 706, a targeted drill guide 600 is coupled to the implant 102. The targeted drill guide comprises a first portion 622 sized and configured to couple to the implant 102 and a second portion 624 extending longitudinally from the first portion 622. The second portion 624 defines a guide hole 626 sized and configure to receive a drill therethrough.

In a fourth step 708, a pilot hole is formed in the bone 114. The pilot hole is formed by inserting a drill 620 through the drill guide hole 626 and into the bone 114. The drill guide 600 positions the drill 620 such that the pilot hole is formed in the bone 114 through the screw hole 110 in the flange 108. The pilot hole extends at an angle through the screw hole 110 and is sized and configured to receive a targeted screw therein. The drill guide 600 is removed from the implant 102 after the pilot hole has been formed.

In a fifth step 710, a targeted screw 112 is inserted into the pilot hole and through the screw hole 110 of the flange 108. The targeted screw 112 extends from at least a first side of the bone 114, through the screw hole 110 of the implant 102, and at least partially into a second side of the bone 114. The targeted screw 112 anchors the implant 102 to the bone 114.

In some embodiments, an implant is disclosed. The implant comprises a body having a bone contact surface and an articulation surface. The body further comprises a first flange extending longitudinally from the bone contact surface, the flange defining a first screw hole configured to receive a targeted screw therethrough.

In some embodiments, the first screw hole is located in a center of the first flange.

In some embodiments, the first flange defines a second screw hole configured to receive a targeted screw therethrough.

In some embodiments, the first screw hole and the second screw hole are horizontally aligned.

In some embodiments, the first flange extends longitudinally from an anterior portion of the body.

In some embodiments, the first flange extends longitudinally from a posterior portion of the body.

In some embodiments, the body further comprises a second flange extending longitudinally from the bone contact surface. The second flange defines a second screw hole configured to receive a targeted screw therethrough.

In some embodiments, the first screw hole in the first flange and the second screw hole in the second flange are aligned such that a single targeted screw passes through the first screw hole and the second screw hole when inserted into a bone.

In some embodiments, the implant comprises a talar dome implant.

In some embodiments, a drill guide is disclosed. The drill guide comprises a first portion configured to couple to an articulation surface of an implant and a second portion extending longitudinally from the first portion. The second portion defines a first drill guide hole sized and configured to receive a drill therethrough.

In some embodiments, when the first portion is coupled to the articulation surface of the implant, the first drill guide hole is positioned such that the drill inserted therethrough is in line with a first screw hole formed in a first flange of the implant.

In some embodiments, the second portion comprises a second drill guide hole sized and configured to receive a drill therethrough.

In some embodiments, when the first portion is coupled to the articulation surface of the implant, the second drill guide hole is positioned such that the drill inserted therethrough is in line with a second screw hole formed in the first flange of the implant.

In some embodiments, when the first portion is coupled to the articulation surface of the implant, the second drill guide hole is positioned such that the drill inserted therethrough is in line with a second screw hole formed in a second flange of the implant.

In some embodiments, a method for coupling an implant to a bone is disclosed. The method comprises locating an implant at a predetermined location of a bone. The implant comprises a body having an articulation surface and a bone contact surface and a first flange extending longitudinally from the bone contact surface, wherein the first flange defines a first screw hole. The method further comprises coupling a drill guide to the implant. The drill guide comprises a first portion configured to couple to the articulation surface of the implant and a second portion extending longitudinally from the first portion. The second portion defines at least one drill guide hole sized and configured to receive a drill therethrough. The method further comprises forming a first screw channel through the bone and the first screw hole by inserting a drill through the drill guide hole.

In some embodiments, the method further comprises removing the drill from the screw channel, uncoupling the drill guide from the implant, and inserting a first screw into the first screw channel and the first screw hole to couple the implant to the bone.

In some embodiments, the first screw channel extends through the bone and into an adjacent bone. The first screw is inserted through the first screw channel in the bone and into the adjacent bone to fuse the bone and the adjacent bone.

In some embodiments, the method further comprises forming a second screw channel through the bone and a second screw hole defined by the first flange by inserting the drill through a second drill guide hole.

In some embodiments, the method further comprises inserting a first targeted screw into the first screw channel and through the first screw hole in the flange and inserting a second targeted screw into the second screw channel and through the second screw hole in the flange.

In some embodiments, the method further comprises forming a second screw channel through the bone and a second screw hole defined by a second flange of the implant by inserting the drill through a second drill guide hole.

Although the subject matter has been described in terms of exemplary embodiments, it is not limited thereto. Rather, the appended claims should be construed broadly, to include other variants and embodiments, which may be made by those skilled in the art.

What is claimed is:

1. An implant system, comprising:
   a talar dome implant, comprising:
      a body having a bone contact surface and an articulation surface, the articulation surface comprising a first hemisphere and a second hemisphere with a groove therebetween; and
      a first flange extending longitudinally from the bone contact surface, the flange defining a first screw hole configured to receive a targeted screw therethrough; and
   a single-piece targeted drill guide comprising a first portion having a curvature and cross-section configured to match a curvature and cross-section of the articulation surface of the implant and a second portion extending longitudinally from the first portion, the second portion defining at least one guide hole therethrough, wherein the guide hole has a predetermined angle through the second portion so that when a drill passes through the guide hole, an axis of the drill passes through the first screw hole formed in the flange.

2. The implant system of claim 1, wherein the first screw hole is located in a center of the first flange.

3. The implant system of claim 1, wherein the first flange defines a second screw hole configured to receive a targeted screw therethrough.

4. The implant system of claim 3, wherein the first screw hole and the second screw hole are horizontally aligned.

5. The implant system of claim 1, wherein the first flange extends longitudinally from an anterior portion of the body.

6. The implant system of claim 1, wherein the first flange extends longitudinally from a posterior portion of the body.

7. The implant system of claim 1, comprising a second flange extending longitudinally from the bone contact surface, the second flange defining a second screw hole configured to receive a targeted screw therethrough.

8. The implant system of claim 7, wherein the first screw hole in the first flange and the second screw hole in the second flange are aligned such that a single targeted screw passes through the first screw hole and the second screw hole when inserted into a bone.

9. A method for coupling an implant to a bone using the system of claim 1, the method comprising:
   locating the implant at a predetermined location of a bone;
   coupling the drill guide to the implant; and
   forming a first screw channel through the bone by inserting a drill through the at least one guide hole and the first screw hole.

10. The method of claim 9, further comprising:
    removing the drill from the screw channel;
    uncoupling the drill guide from the implant; and
    inserting a first screw into the first screw channel and the first screw hole to couple the implant to the bone.

11. The method of claim 10, wherein the first screw channel extends through the bone and into an adjacent bone, and wherein the first screw is inserted through the first screw channel in the bone and into the adjacent bone to fuse the bone and the adjacent bone.

12. The method of claim 9, further comprising forming a second screw channel through the bone by inserting the drill through a second drill guide hole and a second screw hole defined by the first flange.

13. The method of claim 12, further comprising:
    inserting a first targeted screw into the first screw channel and through the first screw hole in the flange; and
    inserting a second targeted screw into the second screw channel and through the second screw hole in the flange.

14. The method of claim 9, further comprising forming a second screw channel through the bone by inserting the drill through a second drill guide hole and a second screw hole defined by a second flange of the implant.

* * * * *